US006277580B1

(12) United States Patent
Ellingson et al.

(10) Patent No.: US 6,277,580 B1
(45) Date of Patent: Aug. 21, 2001

(54) **SPECIES-SPECIFIC GENETIC IDENTIFICATION OF *MYCOBACTERIUM PARATUBERCULOSIS***

(75) Inventors: Jay L. E. Ellingson; Judith R. Stabel, both of Ames, IA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/440,833

(22) Filed: Nov. 15, 1999

Related U.S. Application Data

(62) Division of application No. 09/108,051, filed on Jun. 30, 1998, now Pat. No. 5,985,576.

(51) Int. Cl.$^7$ .............................. C12Q 1/68; C12P 19/34; C07K 14/00

(52) U.S. Cl. .................................. 435/6; 435/91.2; 514/2; 530/350; 536/23.1; 536/23.7; 536/24.3; 536/24.32; 536/24.33

(58) Field of Search ............................... 435/6, 7.2, 7.24; 424/141.1; 530/350; 514/2

(56) References Cited

U.S. PATENT DOCUMENTS 5,314,801 5/1994 Nycz et al. .............................. 435/6

OTHER PUBLICATIONS

Ellingson, J. L. E., Bolin. C. A., Stabel, J. R., Mol. Cell. Probes 12, 133–142 (1998) Identification of a gene unique to *Mycobacterium avium* subspecies paratuberculosis and application to diagnois of paratuberculosis.*

Jay L. E. Ellingson et al., "Identification of a Genetic Element Unique to *Mycbacterium paratuberculosis* and Application to Paratuberculosis Diagnosis" 97th General Meeting, American Society for Microbiology, Miami Beach, May 4–8, 1997.

Jay L. E. Ellingson et al., "Identification of a New Genetic Element Unique to *Mycobacterium paratuberculosis* and Application to Diagnosis of Paratuberculosis", First International Veterinary Vaccines and Diagnostics Conference, Madison, Wisconsin, Jul. 27–31, 1997.

* cited by examiner

*Primary Examiner*—Karen Cochrane Carlson
*Assistant Examiner*—Chih-Min Kam
(74) *Attorney, Agent, or Firm*—M. Howard Silverstein; Curtis P. Ribando; John D. Fado

(57) ABSTRACT

An *M. paratuberculosis* gene referred to as hspX provides a useful target region for the construction of suitable probes and primers that are species-specific for distinguishing *M. paratuberculosis* from related mycobacteria in a test sample. *M. paratuberculosis* is the causative agent of Johne's disease and has been isolated from human patients with Crohn's disease.

6 Claims, 2 Drawing Sheets

5'-ATGTCTGAACCCGGCTACACACCGCCCGACCTGATGCTGGTCGGCGACGACCACG
TGCGCGCATACCGCGAAACCGGCGGCGAGACCGGCTATCTGTGGAACGGCGTTCCG
ATCTTGCTGCTCACGGTGACCGGGCGTCGCACCGGCCGCGCACTCACGTCGGCGCTG
ATCTTCGGCCGCGACGGCGACGACTATCTGGTGGTGGCCTCCATGGGCGGCGCGCCG
*R D G D D*
CGGCAC*CCGTCGTGGTATCTGAATCTGCAAGCCAAT*CCGGCGGCCGGAATTCAGGTG
CAAGCCGACGAGTTGGCGGTCGTGGCGCGCACCGCGTCGGCCGCCGAGAAGCCGCG
GTTTTGGAAGATCATGACTGACGTGTGGCCCAACTACGACGTCTACCAGTCACGAAC
CGACCGCGACATTCCCGTCGTTGTACTCACACCGGCATGA-3'

FIG. 2

SPECIES-SPECIFIC GENETIC IDENTIFICATION OF *MYCOBACTERIUM PARATUBERCULOSIS*

This application is a division of application Ser. No. 09/108,051, filed Jun. 30, 1998, now U.S. Pat. No. 5,985,576.

BACKGROUND OF THE INVENTION

1. Field of the Invention

*Paratuberculosis* poses a significant economic and health problem worldwide, especially in the cattle industry.[1,2] *Mycobacterium avium* subspecies *paratuberculosis*[3] (*M. paratuberculosis* ) is the etiologic agent of *paratuberculosis* (Johne's disease), a chronic granulomatous enteritis of both domestic and wild ruminants. This organism is an intracellular pathogen that replicates within macrophage of both the gastrointestinal tract and associated lymphatic tissues.[4] The disease can be transmitted in utero, to nursing calves, or via infected fecal contamination of food. Diagnosis of subclinical *paratuberculosis* is problematic because infection progresses slowly and infected animals often do not show signs of the disease for years. Once the disease is established in a herd, there is no cure. Annual economic losses to the dairy industry are in the billions of dollars worldwide, primarily as a result of reduced milk production, decreased reproductive efficiency, and death.

In humans, *M. paratuberculosis* has been isolated from patients with Crohn's disease, a chronic enteritis with clinical symptoms similar to animals with *paratuberculosis.*[5,6] *M. paratuberculosis* has been implicated as a possible cause of Crohn's disease, however, the etiology of this disease remains unknown.

This invention relates to a species-specific genetic target element useful for identifying *M. paratuberculosis* and for distinguishing this organism from related bacteria by various diagnostic techniques. Probes and primer sets are disclosed for detecting target sequence in laboratory and clinical samples containing *M. paratuberculosis.*

2. Description of the Prior Art

Cattle shed *M. paratuberculosis* in their feces during the subclinical and clinical stages of infection. Currently, the most sensitive test available for subclinical *paratuberculosis* requires a prolonged 8–12 week fecal culturing of the organism. Existing immunological diagnostic tests are rapid but have disadvantages resulting from poor specificity of the antigens used in the assays.

Nucleic acid diagnostic methodology is used as a rapid and sensitive way to identify specific species of mycobacteria.[7,8,9] Some mycobacterial species are genetically very closely related to *M. paratuberculosis* according to DNA-DNA hybridization analysis.[10] Genome homology ranging from 50% to nearly 100% has been reported between the ATCC 19698 reference strain of *M. paratuberculosis* and species of the *Mycobacterium avium* complex (MAC) which includes the incompletely separated *Mycobacterium avium* (subspecies avium [*M. avium*] and subspecies silvaticum [*M. silvaticum*] and *Mycobacterium intracellulare* as well as other strains not assigned to either species.[11,12,13] *M. paratuberculosis* DNA is also related to DNA of other mycobacteria, such as *Mycobacterium bovis, Mycobacterium leprae,* and *M. tuberculosis.*[14,15] The high percentage of genetic relatedness of *M. paratuberculosis* with other mycobacterial species requires the cloning, sequencing, and characterization of unique genetic markers (genetic elements or genes) to differentiate these closely related species. Species-specific genetic markers are useful tools for the development of new molecular diagnostic tests.

Only two species-specific genetic elements have been identified in the *M. paratuberculosis* genome.[16,17] DNA probes derived from these genetic elements have been used to detect *M. paratuberculosis* infection. One genetic element, IS900, is a 1.45 kbp insertion element found at approximately 20 copies per chromosome.[16] Similar insertion elements, which have sequences related to IS900, have been identified in closely related mycobacteria, such as *M. avium* (IS901)[18,19] and *M. silvaticum* (IS902).[20] The now commercially available IS900 DNA diagnostic kit (IDEXX Corp.), which was used in studies conducted in a *M. paratuberculosis* control program, yields an 89% specificity and a 13% sensitivity.[21]

The other *M. paratuberculosis* species-specific genetic element that has been identified, F57, is a 620 bp DNA fragment not related to any known sequence, including the IS900 insertion element.[17] Southern hybridization analysis using the F57 fragment suggests that this genetic element is single-copy in the *M. paratuberculosis* genome. The F57 genetic element is currently being used as a diagnostic tool to identify *M. paratuberculosis* infection in both cattle and humans (patients with Crohn's disease).[10,17] However, the cloning and sequencing of additional *M. paratuberculosis*-specific genetic elements or genes is needed to improve or develop new rapid and sensitive nucleic acid diagnostic tests for the differentiation of *paratuberculosis* infection.

Currently, there is a need for an accurate, rapid and reliable detection of *M. paratuberculosis* infection.

SUMMARY OF THE INVENTION

We have now discovered a *M. paratuberculosis* gene, hereafter referred to as hspX, that is present as a single-copy gene in the *M. paratuberculosis* genome. This gene provides a useful target region for the construction of suitable probes and primers that are species-specific for distinguishing *M. paratuberculosis* from related mycobacteria in a test sample. Diagnostic assays for *M. paratuberculosis* could also be based on expressed protein products of the hspX gene, such as in an ELISA assay.

In accordance with this discovery, it is an object of the invention to provide a sensitive, specific, and rapid diagnostic tool for positively identifying *M. paratuberculosis* in a clinical or laboratory sample.

It is also an object of the invention to provide a target region for constructing probes and primer sets tailored to the desired specificity for detecting *M. paratuberculosis* infections.

Another object of the invention is to provide an improved method for diagnosing Johne's disease in ruminant animals.

Other objects and advantages of the invention will become readily apparent from the ensuing description.

BRIEF DESCRIPTION OF THE DRAWINGS

FIG. 2 is the hspX open reading frame target sequence of the invention. Bold italics letters depict the MP probe, the ATG start codon is underlined, the TGA stop codon is double underlined, and the deduced amino acid sequence is indicated (amino acid shown below the first nucleotide of each codon).

DEFINITIONS

Figure 1:
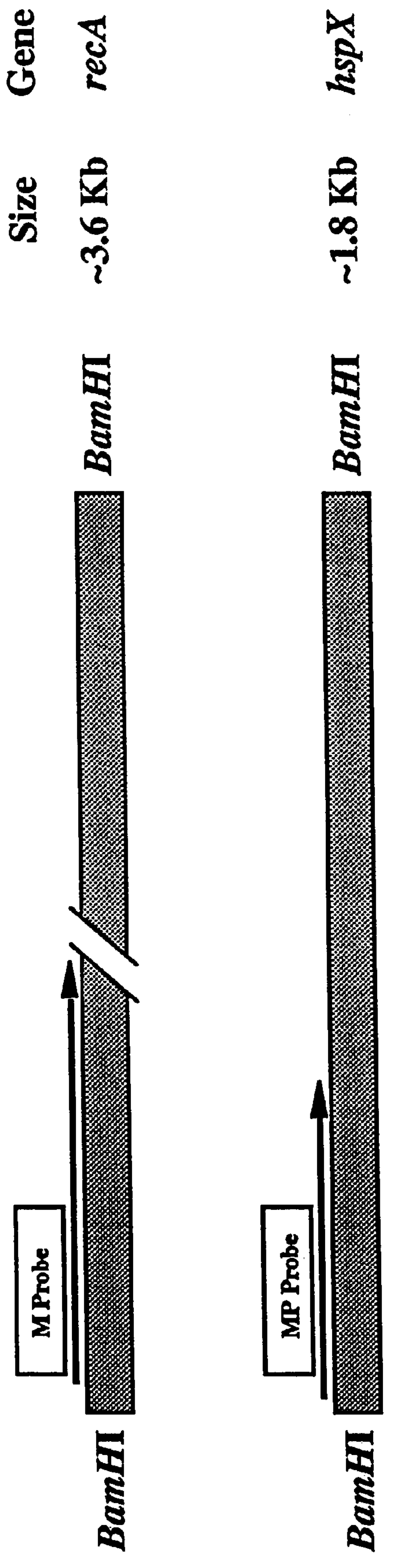
FIG. 1 is a schematic diagram of BamHI restriction fragments containing the hspX and recA open reading frames in *Mycobacterium avium* subspecies genomes. The positions of a *M. paratuberculosis* species-specific DNA probe (MP probe) in the hspX gene of the invention and of the generic mycobacterial DNA probe (M probe) in the recA gene are shown.

As used herein, the expression "test sample" is intended to mean any clinical, laboratory, environmental or other collected sample of material that is suspected of containing the intended target nucleic acid which is to be detected. Exemplary test samples include swabs, scrapings or collections of food, bacteriologic cultures, body fluids, tissues or other sources of mycobacterial infection or contamination.

The expression "target nucleic acid" or "target sequence" is intended to include the sequence within the hspX gene (FIG. 2, SEQ ID NO:1) given below, DNA or RNA sequences complementary to SEQ ID NO:1, and any portion of the aforementioned DNA or RNA sequences that is of sufficient size to permit the desired level of identification.

The term "probe" is used herein in the broadest sense to refer to either a labeled or an unlabeled, single-stranded nucleic acid that will hybridize under predetermined conditions of stringency to the target nucleic acid. Such probes may be DNA or RNA and will typically be at least about 15 bases in length, and preferably about 20–100 bases in length. When used in a hybridization assay, hybrids formed from the probes and the target sequence are usually detected by means of a detectable label affixed directly to the probe. Alternatively, probes can be used as helper probes to facilitate binding of a separate labeled probe to the target nucleotide. It is understood that for hybridization to occur, the probe may or may not be exactly complementary to thetarget sequence, provided that the hybridization conditions are appropriately selected to permit hybridization even when there are a limited number of mismatches between the respective sequences.

The term "primer" is used herein in its usual sense to be descriptive of an oligonucleotide (DNA or RNA), usually about 15–30 nucleotides in length, and preferably about 17–26 bases in length, that will participate in a primer extension reaction when catalyzed by a polymerase. These reactions are more commonly referred to as "polymerase chain reactions" ("PCR"). Contemplated herein as primers are only those nucleotides that are properly oriented so as to amplify a region within the target sequence.

The expression "substantial equivalent thereof" in reference to any target sequence or to the sequence of a probe or primer is intended to mean that minor additions, deletions, or mismatches can be present in the sequence to the extent that such variations do not prevent the hybridization or annealing of the nucleic acids essential to the assay.

"Stringency" refers to the conditions under which hybridization takes place. At high stringency, only exact matches of DNA and/or RNA will hybridize stably. Under low stringency, 80–90% homologous sequences may still hybridize.

Unless otherwise indicated, the term "species-specific" is used herein to indicate specificity for the subspecies *M. paratuberculosis.* The expression "sequence-specific oligonucleotide" is used herein to refer to probes or primers having a hybridizing region that is exactly complementary to a segment of the target region.

DETAILED DESCRIPTION OF THE INVENTION

The target sequence for use in the invention is the *M. paratuberculosis* hspX gene, the complement of said gene, or an RNA transcript of this gene. These target sequences lend themselves to the development of species-specific DNA- or RNA-based diagnostic assays for *M. paratuberculosis* because they are unique to this subspecies.

To initially identify the target sequence, *M. paratuberculosis* genomic DNA was digested with PstI, size fractionated by agarose gel electrophoesis, and screened using an "in-gel" hybridization method with eight 15 bp DNA probes (SEQ ID NOS:5–12) that contained in one open reading frame (ORF) the nucleotide sequence encoding the arginine-glycine-aspartic acid (RGD) peptide adhesion motif. Purified PstI fragments of size ~3.2 kbp and ~3.6 kbp were cloned into the phagemid pBluescript II SK+multiple cloning site and the recombinant plasmids were used to transform *E. coli* ElectroMAX DH10B™ cells by electroporation using standard protocols. [25] Plasmids from about 50 random transformants were screened by DNA hybridization using the degenerate RGD probes to yield two positive recombinant plasmid DNAs designated pBpst101 and pBpst102. These clones were subjected to nucleotide sequence analysis for the purpose of identifying all potential open reading frames.

The pBpst101 clone contains part of an open reading frame (ORF) of 507 nucleotides coding for 169 amino acids (aa) residues from the putative *M. paratuberculosis* recA gene. Comparison of nucleotide and deduced amino acid sequences with known sequences using the BLASTN and BLASTX search algorithms revealed that this partial ORF has significant homology to the conserved 5' terminus of the known ORFs of the recA genes cloned from *M. tuberculosis* and *Mycobacterium leprae.* The closest similarities were found to be the nucleotides of the *M. tuberculosis* and *M. leprae,* 89% and 85% similar, respectively (data not shown). Nucleotide sequence analysis also revealed that the recA portion of this pBpst101 clone was 80% similar to the recA homologue cloned from *Streptomyces venezuelae* ISP5230. From the recA portion of the pBpst101 clone, a 33 bp mycobacterial DNA probe (SEQ ID NO:3), designated M (FIG. 1), was synthesized and used as an internal control probe for detection of mycobacterial genomic DNA.

Clone pBpst102 contains an ORF of 432 nucleotides encoding for 144 amino acid residues (SEQ ID NO:2) for a putative heat-shock-like protein, designated hspX, which is unique to *M. paratuberculosis.* Residues 60–64, arginyl-aspartic acid-glycyl-aspartic acid-aspartic acid (RDGDD) form a conserved peptide motif found in four cloned dnaJ genes including the *Bacillus subtilis* and *M. tuberculosis* dnaJ genes. The BLASTX analysis revealed that the sequences flanking the region encoding the RDGDD motif were unique to *M. paratuberculosis.* From these flanking regions a 30 bp *M. paratuberculosis* species-specific DNA probe (SEQ ID NO:4), designated MP (FIGS. 1 and 2), was selected and synthesized.

When the M probe derived from the recA is tested against genomic DNA extracted from various mycobacteria such as shown in Table I using Southern hybridization analysis, it is able to differentiate mycobacterial species from other pathogenic bacterial species as discussed in further detail in Example 2. The MP probe of the invention, derived from the hspX genomic sequence, is able to differentiate *M. paratuberculosis* from other species (and subspecies) belonging to the *M. avium* complex as also discussed in further detail in Example 2. The observation that the MP sequence is only found in *M. paratuberculosis* species suggests that the open reading frame containing this sequence encodes a protein that is specific to *M. paratuberculosis.*

The strategy for identifying other useful probes or PCR primer sets based on the hspX target region sequence would be in accord with standard guidelines as well-known in the art. Of course, particularly for a short oligomer, the primary consideration would be sequence distinctness within the region being assayed. Other considerations would include the length and the melt temperature ($T_m$) of the selected target region. The methods for construction and use of probes and primers are well-established in the art.

A strategy for constructing an oligonucleotide useful as a probe or primer is initiated by predetermining the length of the oligonucleotide. As previously indicated, probes will typically be at least about 15 bases, and preferably about 20–100 bases, in length. Primers are more typically about 15–30 bases, and preferably about 17–26 bases, in length. The nucleotide sequence complementary to the target DNA or RNA transcript is determined, and the oligodeoxyribonucleotide or oligoribonucleotide is synthesized as the inverse of the complementary sequence. In this way, the probe or primer is in the correct orientation for binding to native nucleic acid in the target sample. Exemplary oligonucleotides useful for purposes of the invention include the 30 bp MP probe described below in Example 2 and the *M. avium* subspecies *paratuberculosis* primers described in Example 3.

In practice of the invention, various assays for *M. paratuberculosis* could be performed. For example, a clinical sample obtained from the test subject would first be cultured under suitable conditions to expand the *M. paratuberculosis* organism, and then a test sample of the resultant culture would be subjected to polymerase chain reaction (PCR). PCR using the hspX primers could also be performed directly on nucleic acids eluted from frozen biopsy tissue sections and/or formalin-fixed paraffin-embedded tissue sections. Amplified nucleic acid fragments can then be detected, for example, by Southern hybridization. Alternatively, clinical samples would be used in a hybridization assay with a labeled probe to indicate the presence of the hspX gene or its RNA transcript.

In an alternative embodiment, the protein expressed by the hspX gene may be used as an immunodiagnostic reagent for binding and detecting antibodies in the serum of an animal. Detection of antibodies against the hspX protein or fragments thereof in the sera of animals may be used for monitoring and detecting animals which are carriers of *M. paratuberculosis* but which do not show outward signs of infection, as well as identifying animals previously exposed or infected with the mycobacterium. A variety of conventional immunoassays are suitable for use herein, although ELISA is preferred. For example, in such an ELISA test, the purified hspX protein may be used as an antigen bound to the wells of a microtiter plate. Following contact of the test animal sera with the adsorbed antigen, bound anti-hspX antibodies may then be detected.

The hspX protein may also be covalently bonded to a non-related fusion protein as described in greater detail hereinbelow. The invention also encompasses substantial equivalents of this protein which retain the ability to elicit antibody production in an animal against *M. paratuberculosis.* The practitioner of ordinary skill in the art will recognize that slight deviations of the amino acid sequences may be made without affecting the immunogenicity of the protein. Substantial equivalents of the above protein include conservative substitutions of amino acids with other amino acids, including either naturally occurring or non-conventional amino acids, which maintain substantially the same charge and hydrophobicity as the original amino acid. Conservative substitutions include for example, replacement of glycine for alanine, valine for isoleucine, leucine for isoleucine, aspartic acid for glutamic acid, lysine for arginine, asparagine for glutamine, phenylalanine for tryptophan, and tryptophan for tyrosine. Examples of conservative substitutions with non-conventional amino acids are described in Rosenberg et al. (U.S. Pat. No. 5,679,782) the contents of which are incorporated by reference herein.

In use, it is envisioned that the isolated protein will typically be formulated in conjunction with a suitable inert carrier or vehicle as known in the art. The skilled practitioner will recognize that such carriers should of course be compatible with the protein. The concentration and amount of the protein in the final composition may vary depending upon the desired use and type of response needed, and the host animal. In any event, the protein should be employed in an amount effective to induce the preferred response as determined by routine testing.

When the protein is used to elicit antibody production against *M. paratuberculosis,* the proteins may be formulated with a physiologically acceptable diluent or carrier such as phosphate buffered saline. The proteins may be administered to a target animal by any convenient route, including intramuscularly, intraperitonealy or preferably subcutaneously, in a single dose or in a plurality of doses. The protein may also be administered in combination with optional stabilizers and immunopotentiating agents or adjuvants. Typical stabilizers include, for example, sucrose, an alkali metal hydrogen phosphate salt, glutamate, serum albumin, gelatin, or casein. A variety of adjuvants are suitable for use herein, although a mixture of alhydrogel and amphigen is preferred. Other conventional adjuvants which may be suitable for use herein include those described by Davis et al. (ed.) (Microbiology, second edition, Harper & Row, Hagerstown, Md., 1973, pp. 480–482), the contents of which are incorporated by reference herein. The proteins may be stored under refrigeration or in frozen or lyophilized form.

In a preferred embodiment, the objective of antibody production is the protection of cattle against *M. paratuberculosis* by eliciting antibody production and/or an immediate-type hypersensitivity in the animal. Generally, the proteins are administered to the target animal in an amount effective to elicit either or both of these responses in a subject animal as compared to an untreated control. The effective amount will vary with the particular target animal, its age and size, and may be readily determined by the practitioner skilled in the art. Without being limited thereto, typical doses for treatment of cattle may be greater than 5 $\mu$g/animal/dose, preferably between 5 to 25 $\mu$g/animal/dose administered by subcutaneous or intramuscular injection.

The antigenic proteins of the invention are produced by growing host cells transformed by the expression vectors described above under conditions whereby the antigen is produced. The antigens are then isolated from the host cells. Depending on the host cell used, transformation is done using standard techniques. For example, the calcium treatment employing calcium chloride, as described by Cohen (1972, Proc Natl Acad Sci USA, 69:2110), or the RbC1 method described in Maniatis et al. (ibid, p. 254) may be used for procaryotes or other cells which contain substantial cell wall barriers. Infection with *Agrobacterium tumefaciens* such as described by Shaw (1983, Gene, 23:315) may be used for certain plant cells. For mammalian cells without such cell walls, the calcium phosphate precipitation method of Graham and Van der Eb (1978, Virology, 52:546) may be used. Transformations into yeast may be conducted, for example, according to the method of Van Solingen, et al., (1977, J. Bacter., 130:946), and Hsiao et al. (1979, Proc Natl Acad Sci USA, 76:3829).

In general, after construction of a suitable expression system, the system is transfected into the appropriate host and successful transformants may be selected by markers contained on the expression vectors. Successfully transformed colonies are then cultured in order to produce the protein. Optionally, a promoter which can be controlled by regulating conditions in the environment may be used such that the cells can be grown under conditions where the gene encoding the desired protein of the invention is not expressed, but production of the protein may be induced by appropriate manipulation of conditions, as described in U.S. Pat. No. 5,670,339. This protocol may be used to prevent premature accumulation of the protein which may be harmful to the growth of the cell.

The protein may be produced intracellularly, or in secreted form by construction of vectors wherein the peptide is preceded by a signal peptide workable in the appropriate host. The recombinant protein may then be recovered from the medium or from the cells using suitable techniques generally known in the art, and purified by, for example, ion exchange chromatography, ammonium sulfate precipitation, or gel permeation chromatography.

In a variation of the above embodiment, the antibodies so-produced in the host animal or monoclonal antibodies raised to the hspX protein may be recovered for use in a diagnostic assay for the identification of *M. paratuberculosis.* A variety of conventional immunoassay techniques are suitable for use herein, including RIA, or ELISA, or double antibody sandwich immunoassays.

The following examples are intended to further illustrate the invention.

EXAMPLE 1

Bacterial Strains, Growth Conditions, and Mycobacterial Identification.

The origin and source of the 41 mycobacterial strains, including 28 mycobacterial strains, used in this study are listed in Table I, below.

Primary *Mycobacterium avium* complex isolates were obtained by conventional bacteriological culture and were identified by growth characteristics and mycobactin dependence (with all *M. paratuberculosis* isolates being mycobactin J-dependent). The cultures were passed and grown at 37° C. to late exponential phase ($A_{540}$=0.2) in 150-$cm^2$ tissue culture flasks containing 75 ml of Middlebrook 7H9 liquid medium (pH 5.9) supplemented with Dubos oleic albumin complex enrichment, 0.05% Tween 80, and ferric mycobactin J. Subsequently, D-cycloserine (1 mg/ml final concentration) was added to each flask, mixed thoroughly, and cultures were incubated for an additional 24 h. The cell cultures were then harvested by centrifugation (11,000×g for 30 min at 10° C.).

*Escherichia coli* ElectroMAX DH10B™ cells (Gibco BRL: Life Technologies, Inc.) were used as the host strain for recombinant plasmids. Working cultures of *E. coli* were grown in Luria-Bertani broth (LB) and maintained on LB agar plates.[22] Stock cultures were stored in LB supplemented with 20% glycerol at −80° C.

DNA Isolation, Plasmids, and Cloning Procedures.

Genomic DNA was extracted from mycobacteria (*M. avium, M. intracellulare, M. paratuberculosis* and *M. silvaticum*) by the method described by Whipple et al.[23], as modified by Bauerfeind et al.[24] Mycobacterial cells were harvested (~100 mg, wet weight), washed in TE buffer (10 mM Tris-HCl, 1 mM EDTA [pH 8.0]), and incubated in TE buffer containing 16,000 U/ml (final concentration) of lipase for 2 h at 37° C. Lysozyme (5 mg/ml) was then added to the solution and incubation was continued for an additional 2 h at 37° C. The samples were then treated with proteinase K (2 mg/ml) and sodium dodecyl sulfate (10 mg/ml) and incubated for an additional 15 h at 50° C. Following the incubation, ½ volume of 7.5 M potassium acetate was gently mixed into each sample, the samples were placed on ice for 10 min, and centrifuged for 10 min at 4° C. Subsequently, DNA was purified from the supernatant by repeated phenol-chloroform-isoamyl alcohol (25:24:1; vol/vol/vol) extraction and was precipitated by adding 2 volumes of 95% ethanol. Precipitated DNA was washed with 70% ethanol, dried, and resuspended in sterile ultrapure water.

*M. paratuberculosis* genomic DNA was digested with PstI, size fractionated by agarose gel electrophoresis, and screened using an "in-gel" hybridization method with eight 15 bp DNA probes (5'-GCACGGGGCGACGTC-3', 5'-GCACGGGGGGACGTC-3', 5'-GCACGCGGCGACGTC-3', 5'-GCACGAGGCGACGTC-3', 5'-GCACGCGGGGACGTC-3', 5'-GCACGGGGGGACGTC-3', 5'-GCAAGAGGGGACGTC-3', 5'-GCAAGGGGGGACGTC-3'; SEQ ID NOS:5–12, respectively) that contained in one open reading frame the nucleotide sequence encoding the RGD peptide adhesion motif.[25] PstI restriction fragments of size ~3.2 kb and ~3.6 kb were isolated and purified by the 1% agarose "gel trough" method.[19] Purified PstI fragments were cloned into the phagemid pBluescript II SK+multiple cloning site and the recombinant plasmids were used to transform *E. coli* ElectroMAX DH10B™ cells by electroporation using standard protocols.[25] Plasmids from ~50 random transformants were screened by DNA hybridization using the degenerate RGD probes. The positive recombinant plasmid DNAs were isolated and purified by using alkaline-lysis/polyethylene glycol (PEG) precipitation[22] and were designated pBpst101 and pBpst102, respectively.

DNA Sequence Analysis and Identification of Mycobacterial Genes.

Nucleotide sequences were determined by dye chain termination reactions on Applied Biosystems instrument and sequence scan software at the Iowa State University Nucleic Acid Sequencing Facility (Ames, Iowa). Sequencher™ (Gene Codes, Ann Arbor, Mich.) software was used to align all sequences into a contiguous DNA fragment and to determine all potential open reading frames. Sequence data analysis was done by screening National Center for Biotechnology Information, National Library of Medicine, Bethesda, Md., databases using BLASTN and BLASTX algorithms[26] via the BLAST Network Service.

EXAMPLE 2

Detection of the Genus Mycobacterium and the Species *M. paratuberculosis* by Dioligonucleotide Hybridization analysis.

Purified bacterial genomic DNA from the bacterial strains in Table I was digested with BamHI, BglII, PstI, PvuII, XbaI, or XhoI at 37° C. for 3 h. DNA fragments were separated by electrophoresis-through (11×14 cm or 20×25 cm) 0.8% agarose gels in Tris-borate-EDTA buffer (pH 8.3) at 25 V·18 h or 45 V·20 h, respectively. Hybridization was carried out at 65° C. in 5×SSC containing 0.1% (w/v) N-lauroylsarcosine and 0.02% (w/v) sodium laurylsulfate (1×SSC is 0.15 M NaCl and 0.015 M sodium citrate); the membrane was washed twice in 0.5×SSC–0.1% SDS at 25° C. for 15 min followed by two washes in 0.1×SSC–0.1% SDS at 65° C. for 15 min.

The M Probe

The M probe (33 bp, 5'-GACACCGATTCGCTGCTGGTCAGCCAG CCGGAC-3' (SEQ ID NO:3), mycobacterial recA probe) end-labeled with digoxigenin detectable by chemiluminescence was used in Southern hybridization analysis to identify sequences present in various mycobacterial species. In the initial experiments, the M probe was tested against genomic DNA extracted from various mycobacteria (Table 1). The DNA was digested with BamHI or PvuII (positive controls, only *M. bovis* and *M. tuberculosis*) and hybridized in Southern blots with the M probe. When genomic DNA isolated from *M. bovis* and *M. tuberculosis* was digested with PvuII and hybridized with the M probe only the 2.7 kbp restriction fragment carrying the entire recA gene was present. However, when genomic DNA isolated from *M. bovis* and *M. tuberculosis* was digested with BamHI and hybridized with the M probe only the expected 1.4 kbp restriction-fragment was identified. Only the 1.4 kbp restriction fragment was present because the BamHI restriction sites are internal to the recA ORF and the M probe was designed to be positioned between BamHI restriction sites of the cloned *M. tuberculosis* recA gene.[27] When genomic DNA isolated from *M. avium, M. intercellulare, M. paratuberculosis,* and *M. silvaticum* was digested with BamHI and hybridized with the M probe, restriction fragments of sizes 3.6 kbp, 4.0 kbp, 3.6 kbp, and 3.6 kbp, respectively, were present.

The MP Probe

The MP probe (30 bp, 5'-CCGTCGTGGTATCTGAATCTGCAAGCC AAT-3' (SEQ ID NO:4), *M. paratuberculosis* species-specific probe) end-labeled with digoxigenin detectable by chemiluminescence was used in Southern hybridization analysis to identify sequences present only in the *M. paratuberculosis* genome. In this experiment the MP probe was tested against genomic DNA extracted from various mycobacteria (Table 1). The DNA was digested with BamHI or PvuII and hybridized in Southern blots with the MP probe. When genomic DNA isolated from *M. avium, M. bovis, M. intercellulare, M. silvaticum,* and *M. tuberculosis* digested with BamHI or PvuII was hybridized with the MP probe no restriction fragments carrying this sequence was present. However, when genomic DNA isolated from *M. paratuberculosis* was digested with BamHI and hybridized with the MP probe, a 1.8 kbp restriction fragment was present.

Dioligonucleotide hybridization (M probe and MP probe in the same hybridization solution) was used in Southern analysis to identify sequences present in mycobacteria, specifically sequences in the *M. paratuberculosis* genome. In the initial experiments the dioligonucleotide hybridization (dOH) solution was tested against genomic DNA extracted from various mycobacteria (Table 1). When genomic DNA isolated from *M. avium, M. bovis, M. intercellulare,* and *M. tuberculosis* was hybridized with the dOH solution only the expected restriction fragments carrying the M probe sequence were present. However, when genomic DNA isolated from *M. paratuberculosis* was digested with BamHI and hybridized with the dOH solution, restriction fragments of sizes 3.6 kbp (M probe) and 1.8 kbp (MP probe) were present.

EXAMPLE 3

Detection of the Species *Mycobacterium avium* and the Subspecies *Paratuberculosis* by PCR Analysis Purified mycobacterial genomic DNA listed in Table 2, below, was amplified by PCR using oligonucleotide primers (SEQ ID NO:13 and SEQ ID NO:14) derived from the 16S rRNA (*M. avium* species) sequence and to the unique *M. avium* subspecies *paratuberculosis* hspX gene sequence (SEQ ID NO:15 and SEQ ID NO:16). Amplified DNA fragments were separated by electrophoresis through 20×25 cm 1.5% agarose gels in Tris-borate-EDTA buffer (pH 8.3) at 115 V for 2 h and the DNA product was detected by staining with ethidium bromide. Briefly, amplification products were analyzed by electrophoresing a 12.5 μl —sample in 1.5% agarose gel and staining the DNA with ethidium bromide, the amplified product size was compared with positive control DNA; and if the product was the same molecular weight the amplified DNA product was considered positive. DNA samples that had bands at any other molecular weight position or that had no bands were considered negative. Amplification reactions were performed using a hot start method with a standard 50 μl buffer (pH 8.0) containing the following: 1.5 mM or 2.5 mM Mg2+, 20 pM of each primer, 1.25 U DNA polymerase, and 0.2 mM nucleotides. The oligonucleotide primers used to identify species *M. avium* and the subspecies *paratuberculosis* were derived from 16S rRNA (*M. avium*) sequence and the hspX gene (*paratuberculosis*) sequence, respectively. Primers used to identify the species *M. avium* produced a 180-bp fragment from 16S rRNA sequence and the primers used to identify the subspecies *paratuberculosis* produced a 271-bp fragment from the hspX sequence. Amplification conditions for the 16S rRNA primers included an initial denaturation at 94° C. for 10 min, 50 cycles of 60 sec at 94° C., 15 sec at 65° C. and 60 sec at 72° C., and a final 10-min extension at 72° C. Amplification conditions for the hspX primers included an initial denaturation at 94° C. for 10 min, 50 cycles of 60 sec at 94° C., 60 sec at 60° C. and 60 sec at 72° C., and a final 10-min extension at 72° C.

PCR analysis using the primers derived from the 16S rRNA sequence identified 20/20 (100%) *M. avium* and the primers derived from the hspX gene sequence specifically identified 14/14 (100%) reference (ATCC 19698), bovine, and human isolates of the subspecies *paratuberculosis* (Table 2). The *M. paratuberculosis*-specific primers distinguished *M. paratuberculosis* isolates from related mycobacteria, including all closely related members of the *Mycobacterium avium* subspecies tested in this study. The experiments indicate that the PCR analysis is a useful diagnostic tool to detect mycobacterial infection, specifically *M. paratuberculosis.*

TABLE 1

Bacterial strains used to determine the specificity of the M probe and the MP probe

| Bacteriai strain (Serotype) | Source[a] | Origin[b] | M Probe | MP Probe |
|---|---|---|---|---|
| *M. paratuberculosis* 19698[c] | ATCC | Bovine | + | + |
| *M. paratuberculosis* BEN 43544 | ATCC | Human | + | + |
| *M. paratuberculosis* LINDA 43015 | ATCC | Human | + | + |
| *M. paratuberculosis* 1003 | NADC | Bovine | + | + |
| *M. paratuberculosis* 1004 | NADC | Bovine | + | + |
| *M. paratuberculosis* 1010 | NADC | Bovine | + | + |
| *M. paratuberculosis* 1018 | NADC | Bovine | + | + |
| *M. paratuberculosis* 1026 | NADC | Bovine | + | + |
| *M. paratuberculosis* 1036 | NADC | Bovine | + | + |
| *M. paratuberculosis* 1113 | NADC | Bovine | + | + |
| *M. paratuberculosis* 1425 | NADC | Ovine | + | + |
| *M. paratuberculosis* 1434 | NADC | Ovine | + | + |
| *M. paratuberculosis* 4090 | NADC | Bovine | + | + |
| *M. paratuberculosis* KAY | NADC | Bovine | + | + |
| *M. avium* 18 (Ser. 2)[d] | NADC | Bovine | + | − |
| *M. avium* 25291 (Ser. 2)[c] | ATCC | Chicken | + | − |

TABLE 1-continued

Bacterial strains used to determine the specificity of the M probe and the MP probe

| Bacteriai strain (Serotype) | Source[a] | Origin[b] | M Probe | MP Probe |
|---|---|---|---|---|
| *M. avium* 2264 (Ser. 8) | NVSL | Bovine | + | – |
| *M. avium* subsp. *silvaticum* M21 | NADC | Wood Pigeon | + | – |
| *M. avium* 23667-2625 | NVSL | Bovine | + | – |
| *M. avium* 27183-3013 | NVSL | Swine | + | – |
| *M. bovis* 1145 | NVSL | Bovine | + | – |
| *M. bovis* 2045 | NVSL | Bovine | + | – |
| *M. bovis* TMC401 35720 | ATCC | Bovine | + | – |
| *M. bovis* BCG Pasteur 35734 | ATCC | Bovine | + | – |
| *M. intracellulare* 35772 (Ser. 19)[c] | ATCC | Human | + | – |
| *M. intracellulare* 35764 (Ser. 20) | ATCC | Human | + | – |
| *M. tuberculosis* H37Rv 27294 | ATCC | Human | + | – |
| *M. tuberculosis* H37Ra 25177 | ATCC | Human | + | – |
| *B. bronchiseptica* Human 1 | NADC | Human | – | – |
| *B. bronchiseptica* Dog 1 | NADC | Canine | – | – |
| *B. bronchiseptica* Rat 1 | NADC | Rat | – | – |
| *B. pertussis* | NADC | Human | – | – |
| *B. abortus* 2308 | NADC | Bovine | – | – |
| *E. coli* O157:H7 3081 | NADC | Bovine | – | – |
| *E. coli* O157:H7 3100 | NADC | Bovine | – | – |
| *E. coli* O157:H7 43888 | ATCC | Human | – | – |
| *L. interrogans* | NADC | Bovine | – | – |
| *S. aureus* | NADC | NA | – | – |
| *P. haemolytica* D153 | NADC | Ovine | – | – |
| *P. multocida* | NADC | NA | – | – |
| *Y. enterocolitica* | NADC | NA | – | – |

[a]Source of bacterial strains were as follows: ATCC, American Type Culture Collection (Rockville, MD); NADC, National Animal Disease Center (Ames, IA); NVSL, National Veterinary Services Laboratory (Ames, IA).
[b]Origin: NA, Not Available.
[c]ATCC bacterial type strain.
[d]Formerly *M. paratuberculosis* 18.
M., Mycobacterium; B., Bordetella; *B. abortus, Brucella abortus;* E., Escherichta; L., Leptospira; S., Staphylococcus; P., Pasteurella; Y., Yersina.

TABLE 2

Bacterial strains used to determine the specificity of *M. avium* subspecies [16S rRNA] primers and the *M. avium* subspecies-specific *paratuberculosis* [hspX] primers.

| Bacterial Strain (Serotype) | Source[a] | Origin | 16S rRNA Primers | hspX Primers |
|---|---|---|---|---|
| *M. paratuberculosis* 19698[b] | ATCC | Bovine | + | + |
| *M. paratuberculosis* BEN 43544 | ATCC | Human | + | + |
| *M. paratuberculosis* LINDA 43015 | ATCC | Human | + | + |
| *M. paratuberculosis* 1003 | NADC | Bovine | + | + |
| *M. paratuberculosis* 1004 | NADC | Bovine | + | + |
| *M. paratuberculosis* 1010 | NADC | Bovine | + | + |
| *M. paratuberculosis* 1018 | NADC | Bovine | + | + |
| *M. paratuberculosis* 1026 | NADC | Bovine | + | + |
| *M. paratuberculosis* 1036 | NADC | Bovine | + | + |
| *M. paratuberculosis* 1113 | NADC | Bovine | + | + |
| *M. paratuberculosis* 1425 | NADC | Ovine | + | + |
| *M. paratuberculosis* 1434 | NADC | Ovine | + | + |
| *M. paratuberculosis* 4090 | NADC | Bovine | + | + |
| *M. paratuberculosis* KAY | NADC | Bovine | + | + |
| *M. avium* 18 (Ser. 2)[c] | NADC | Bovine | + | – |
| *M. avium* 25291 (Ser. 2)[b] | ATCC | Chicken | + | – |
| *M. avium* 2264 (Ser. 8) | NVSL | Bovine | + | – |
| *M. avium* subsp. *silvaticum* M21 | NADC | Wood Pigeon | + | – |
| *M. avium* 23667-2625 | NVSL | Bovine | + | – |
| *M. avium* 27183-3013 | NVSL | Swine | + | – |
| *M. bovis* 1145 | NVSL | Bovine | – | – |
| *M. bovis* 2045 | NVSL | Bovine | – | – |
| *M. bovis* TMC401 35720 | ATCC | Bovine | – | – |
| *M. bovis* BCG Pasteur 35734 | ATCC | Bovine | – | – |
| *M. intracellulare* 35772 (Ser. 19)[b] | ATCC | Human | – | – |

TABLE 2-continued

Bacterial strains used to determine the specificity of *M. avium* subspecies [16S rRNA] primers and the *M. avium* subspecies-specific *paratuberculosis* [hspX] primers.

| Bacterial Strain (Serotype) | Source[a] | Origin | 16S rRNA Primers | hspX Primers |
|---|---|---|---|---|
| *M. intracellulare* 35764 (Ser. 20) | ATCC | Human | – | – |
| *M. tuberculosis* H37Rv 27294[b] | ATCC | Human | – | – |
| *M. tuberculosis* H37Ra 25177 | ATCC | Human | – | – |

[a]Source of bacterial strains were as follows: ATCC, American Type Culture Collection (Rockville, MD); NADC, National Animal Disease Center (Ames, IA); NVSL, National Veterinary Services Laboratory (Ames, IA).
[b]ATCC bacterial type strain.
[c]Formerly *M. paratuberculosis* 18.

REFERENCES

1. McNab, W. B, Meek, A. H., Duncan, J. R., Brooks, B. W., Sugden, E. A. (1991a). An evaluation of selected screening tests for bovine paratuberculosis. *Canadian Journal of Veterinary Research* 55, 252–259.
2. McNab, W. B, Meek, A. H., Martin, S. W., & Duncan, J. R. (1991b). Associations between dairy production indices and lipoarabinomannan enzyme-immunoassay results for paratuberculosis. *Canadian Journal of Veterinary Research* 55, 356–361.
3. Thorel, M., Krichevsky, M. & Vincent Levy-Frebault V. (1990). Numerical taxonomy of mycobactin-dependent mycobacteria, emended description of *Mycobacterium avium* subsp. *avium* subsp. nov., *Mycobacterium avium* subsp. *paratuberculosis* subsp. nov., and *Mycobacterium avium* subsp. *silvaticum* subsp. nov. Int. *J. Syst. Bacteriology* 40, 254–260.
4. Chiodini, R. J., Kruiningen, H. J., & Merkal, R. S. (1984). Ruminant *paratuberculosis* (Johne's disease): the current status and future prospects. *Cornell Vet.* 74, 218–262.
5. Chiodini, R. J., Kruiningen, H. J., Thayer, W. R., & Coutu, J. A. (1986). The spheroplastic phase of mycobacteria isolated from patients with Crohn's disease. *J. Clin. Microbiol.* 24, 357–363.
6. McFadden, J. J., Butcher, P. D., Chiodini, R., & Hermon-Taylor, J. (1987). Crohn's disease-isolated mycobacteria are identical to *Mycobacterium paratuberculosis,* as determined by DNA probes that distinguish between mycobacterium species. *J. Clin. Microbiol.* 25, 796–801.
7. Vary, C. P. H., Anderson, P. R., Green, E., Hermon-Taylor, J., & McFadden, J. J. (1990). Use of highly specific DNA probes and the polymerase chain reaction to detect *Mycobacterium paratuberculosis* in Johne's disease. *J. Clin. Microbiol.* 28, 268–275.
8. Mazurek, G. H., Hartman, S., Shang, Y., Brown, B. A., Hector, J. S. R., Murphy, D., & Wallace Jr., R. H. (1993). Large DNA restriction fragment polymorphism in the *Mycobacterium avium*-M. intracellulare complex: a potential epidemiological tool. *J. Clin. Microbiol.* 31, 390–394.
9. Collins, D. M., Erasmuson, S. K., Stephens, D. M., Yates, G. F., & De Lisle, G. W. (1993). DNA fingerprinting of *Mycobacterium bovis* strains by restriction fragment analysis and hybridization with insertion elements IS1081 and IS6110. *J. Clin. Microbiol.* 31, 1143–1147.
10. Cocito, C., Gilot, P., Coene, M., De Kessel, M., Poupart, P., & Vannuffel, P. (1994). *Paratuberculosis. Clin. Microbiol. Rev.* 7, 328–345.
11. Inderlied, C. B., Kemper, C. A., & Bermudez, L. E. M. (1993). The *Mycobacterium avium* complex. *Clin. Microbiol. Rev.* 6, 266–310.

12. McFadden, J. J., Butcher, P. D., Chiodini R., & Hermon-Taylor, J. (1987). Crohn's disease-isolated mycobacteria are identical to *Mycobacterium paratuberculosis,* as determined by DNA probes that distinguish between mycobacterial species. *J. Clin. Microbiol.* 25, 796–801.

13. Yoshimura, H. H., & Graham, D. Y. (1988). Nucleic acid hybridization studies of mycobactin-dependent mycobacteria. *J. Clin. Microbiol.* 26, 1309–1312.

14. Hurley, S. S., Splitter, G. A., & Welch, R. A. (1988). Deoxyribonucleic acid relatedness of *Mycobacterium paratuberculosis* to other members of the family Mycobacteriaceae. *Int. J. Syst. Bacteriol.* 38, 143–146.

15. Imaeda, T., Browslawski, G., & Imaeda, S. (1988). Genomic relatedness among mycobacterial species by nonisotopic blot hybridization. *Int. J. Syst. Bacteriol.* 38, 151–156.

16. Green, E. P., Tizard, M. L., Moss, M. T., Thompson, J., Winterbourne, D. J., McFadden, J. J., & Herman-Taylor, J. (1989). Sequence and characteristics of IS900, an insertion element identified in a human Crohn's disease isolate of *Mycobacterium paratuberculosis. Nucleic Acids Res.* 17, 9063–9073.

17. Poupart, P., Coene, M., Van Hueverswyn, H. & Cocito, C. (1993). Preparation of a specific RNA probe for detection of *Mycobacterium paratuberculosis* and diagnosis of Johne's disease. *J. Clin. Microbiol.* 31, 1601–1605.

18. Kunze, Z. M., Portaels, F., & McFadden, J. J. (1992). Biologically distinct subtypes of *Mycobacterium avium* differ in possession of insertion sequence IS901. *J. Clin. Microbiol.* 30, 2366–2372.

19. Kunze, M. F., Wall, S., Appelberg, R., Silva, M. T., Portaels, F., & McFadden, J. J. (1991). IS901, a new member of a wide-spread class of atypical insertion sequence, is associated with pathogenesis in *Mycobacterium avium. Mol. Microbiol.* 5, 2265–2272.

20. Moss, M. T., Malik, Z. P., Tizard, M. L. V., Green, E. P., Sanderson, J. D., & Hermon-Taylor, J. (1992). IS902, an insertion element of the chronic-enteritis-causing *Mycobacterium avium* subsp. *silvaticum. J. Gen. Microbiol.* 138, 139–145.

21. Van der Griessen, J. W. B., Haring, R. M., Vauclare, E., Eger, A., Haagsma, J., & van der Zeijst, B. A. M. (1992). Evaluation of the abilities of three diagnostic tests based on the polymerase chain reaction to detect *Mycobacterium paratuberculosis* in cattle: application to control program. *J. Clin. Microbiol.* 30, 1216–1219.

22. Sambrook, J., Fritsch, E. F., & Maniatis, T. (1989). Molecular Cloning: a laboratory manual. Cold Spring Harbor, N.Y.: Cold Spring Harbor Laboratory Press.

23. Whipple, D. L., Le Febvre, R. B., Andrews, R. E., & Thiermann, A. B. (1987). Isolation and analysis of restriction endonuclease digestive patterns of chromosomal DNA from *Mycobacterium paratuberculosis* and other Mycobacterium species. *J. Clin. Microbiol.* 25, 1511–1515.

24. Bauerfeind, R., Benazzi, S., Weiss, R., Schliesser, T., Willems, H., & Galjer, G. (1996). Molecular characterization of *Mycobacterium paratuberculosis* isolates from sheep, goats, and cattle by hybridization with a DNA probe to insertion element IS900. *J. Clin. Microbial.* 34, 1617–1621.

25. Wells, J. M., Ellingson, J. L. E., Catt, D. M., Berger, P. J., & Karrer, K. M. (1994). A small family of elements with long repeats is located near sites of developmentally regulated DNA rearrangement in *Tetrahymena thermophila. Mol. Cell. Biol.* 14, 5939–5949.

26. Altschul, S. F., Gish, W., Miller, W., Myers, E. W., & Lipman, D. J. (1990). Basic local alignment search tool. *J. Mol. Biol.* 215, 403–410.

27. Davis, E. O., Sedgwick, S. G. & Colston, M. J. (1991). Novel structure of the recA locus of *Mycobacterium tuberculosis* implies processing of the gene product. *J. Bacteriol.* 173, 5653–5662.

---

We claim:

1. An isolated protein comprising the amino acid sequence of SEQ ID NO:2 or a substantial equivalent thereof, wherein said equivalent consists of one or more conservative amino acid substitution and is effective for eliciting antibody production or local immediate-type hypersensitivity in a mammal against *M. paratuberculosis.*

2. An isolated *Mycobacterium paratuberculosis* hspX protein or substantial equivalent thereof, wherein said equivalent consists of one or more conservative amino acid substitution and retains the ability to elicit in an animal antibody production or a hypersensitivity response.

3. The protein of claim 2 wherein said conservative amino acid substitution comprises a naturally-occurring amino acid.

4. The protein of claim 2 in combination with a carrier.

5. The protein of claim 4, wherein said carrier is a physiologically acceptable diluent or carrier.

6. The protein of claim 4, wherein said carrier is a solid support.

* * * * *

```
                      SEQUENCE LISTING


(1) GENERAL INFORMATION:

   (iii) NUMBER OF SEQUENCES: 16


(2) INFORMATION FOR SEQ ID NO:1:

     (i) SEQUENCE CHARACTERISTICS:
          (A) LENGTH: 435 base pairs
          (B) TYPE: nucleic acid
          (C) STRANDEDNESS: single
          (D) TOPOLOGY: linear

    (ii) MOLECULE TYPE: DNA (genomic)

   (iii) HYPOTHETICAL: NO

    (iv) ANTI-SENSE: NO

    (vi) ORIGINAL SOURCE:
          (A) ORGANISM: Mycobacterium avium subspecies
               paratuberculosis

    (ix) FEATURE:
          (A) NAME/KEY: CDS
          (B) LOCATION: 1..432
```

-continued

```
    (xi) SEQUENCE DESCRIPTION: SEQ ID NO:1:

ATG TCT GAA CCC GGC TAC ACA CCG CCC GAC CTG ATG CTG GTC GGC GAC        48
Met Ser Glu Pro Gly Tyr Thr Pro Pro Asp Leu Met Leu Val Gly Asp
  1               5                  10                  15

GAC CAC GTG CGC GCA TAC CGC GAA ACC GGC GGC GAG ACC GGC TAT CTG        96
Asp His Val Arg Ala Tyr Arg Glu Thr Gly Gly Glu Thr Gly Tyr Leu
             20                  25                  30

TGG AAC GGC GTT CCG ATC TTG CTG CTC ACG GTG ACC GGG CGT CGC ACC       144
Trp Asn Gly Val Pro Ile Leu Leu Leu Thr Val Thr Gly Arg Arg Thr
         35                  40                  45

GGC CGC GCA CTC ACG TCG GCG CTG ATC TTC GGC CGC GAC GGC GAC GAC       192
Gly Arg Ala Leu Thr Ser Ala Leu Ile Phe Gly Arg Asp Gly Asp Asp
     50                  55                  60

TAT CTG GTG GTG GCC TCC ATG GGC GGC GCG CCG CGG CAC CCG TCG TGG       240
Tyr Leu Val Val Ala Ser Met Gly Gly Ala Pro Arg His Pro Ser Trp
 65                  70                  75                  80

TAT CTG AAT CTG CAA GCC AAT CCG GCG GCC GGA ATT CAG GTG CAA GCC       288
Tyr Leu Asn Leu Gln Ala Asn Pro Ala Ala Gly Ile Gln Val Gln Ala
                 85                  90                  95

GAC GAG TTG GCG GTC GTG GCG CGC ACC GCG TCG GCC GCC GAG AAG CCG       336
Asp Glu Leu Ala Val Val Ala Arg Thr Ala Ser Ala Ala Glu Lys Pro
            100                 105                 110

CGG TTT TGG AAG ATC ATG ACT GAC GTG TGG CCC AAC TAC GAC GTC TAC       384
Arg Phe Trp Lys Ile Met Thr Asp Val Trp Pro Asn Tyr Asp Val Tyr
        115                 120                 125

CAG TCA CGA ACC GAC CGC GAC ATT CCC GTC GTT GTA CTC ACA CCG GCA       432
Gln Ser Arg Thr Asp Arg Asp Ile Pro Val Val Val Leu Thr Pro Ala
    130                 135                 140

TGA                                                                   435


(2) INFORMATION FOR SEQ ID NO:2:

     (i) SEQUENCE CHARACTERISTICS:
          (A) LENGTH: 144 amino acids
          (B) TYPE: amino acid
          (D) TOPOLOGY: linear

    (ii) MOLECULE TYPE: protein

    (xi) SEQUENCE DESCRIPTION: SEQ ID NO:2:

Met Ser Glu Pro Gly Tyr Thr Pro Pro Asp Leu Met Leu Val Gly Asp
  1               5                  10                  15

Asp His Val Arg Ala Tyr Arg Glu Thr Gly Gly Glu Thr Gly Tyr Leu
             20                  25                  30

Trp Asn Gly Val Pro Ile Leu Leu Leu Thr Val Thr Gly Arg Arg Thr
         35                  40                  45

Gly Arg Ala Leu Thr Ser Ala Leu Ile Phe Gly Arg Asp Gly Asp Asp
     50                  55                  60

Tyr Leu Val Val Ala Ser Met Gly Gly Ala Pro Arg His Pro Ser Trp
 65                  70                  75                  80

Tyr Leu Asn Leu Gln Ala Asn Pro Ala Ala Gly Ile Gln Val Gln Ala
                 85                  90                  95

Asp Glu Leu Ala Val Val Ala Arg Thr Ala Ser Ala Ala Glu Lys Pro
            100                 105                 110

Arg Phe Trp Lys Ile Met Thr Asp Val Trp Pro Asn Tyr Asp Val Tyr
        115                 120                 125

Gln Ser Arg Thr Asp Arg Asp Ile Pro Val Val Val Leu Thr Pro Ala
    130                 135                 140
```

-continued (2) INFORMATION FOR SEQ ID NO:3:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Mycobacterium avium subspecies paratuberculosis (xi) SEQUENCE DESCRIPTION: SEQ ID NO:3:

GACACCGATT CGCTGCTGGT CAGCCAGCCG GAC 33

(2) INFORMATION FOR SEQ ID NO:4:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Mycobacterium avium subspecies paratuberculosis (xi) SEQUENCE DESCRIPTION: SEQ ID NO:4:

CCGTCGTGGT ATCTGAATCT GCAAGCCAAT 30

(2) INFORMATION FOR SEQ ID NO:5:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Mycobacterium avium subspecies paratuberculosis (xi) SEQUENCE DESCRIPTION: SEQ ID NO:5:

GCACGGGGCG ACGTC 15

(2) INFORMATION FOR SEQ ID NO:6:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (genomic)

-continued (iii) HYPOTHETICAL: NO (iv) ANTI-SENSE: NO (vi) ORIGINAL SOURCE:
(A) ORGANISM: Mycobacterium avium subspecies paratuberculosis (xi) SEQUENCE DESCRIPTION: SEQ ID NO:6:

GCACGGGGGG ACGTC 15

(2) INFORMATION FOR SEQ ID NO:7:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Mycobacterium avium subspecies paratuberculosis (xi) SEQUENCE DESCRIPTION: SEQ ID NO:7:

GCACGCGGCG ACGTC 15

(2) INFORMATION FOR SEQ ID NO:8:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Mycobacterium avium subspecies paratuberculosis (xi) SEQUENCE DESCRIPTION: SEQ ID NO:8:

GCACGAGGCG ACGTC 15

(2) INFORMATION FOR SEQ ID NO:9:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Mycobacterium avium subspecies paratuberculosis (xi) SEQUENCE DESCRIPTION: SEQ ID NO:9:

-continued

```
GCACGCGGGG ACGTC                                                      15


(2) INFORMATION FOR SEQ ID NO:10:

     (i) SEQUENCE CHARACTERISTICS:
          (A) LENGTH: 15 base pairs
          (B) TYPE: nucleic acid
          (C) STRANDEDNESS: single
          (D) TOPOLOGY: linear

    (ii) MOLECULE TYPE: DNA (genomic)

   (iii) HYPOTHETICAL: NO

    (iv) ANTI-SENSE: NO

    (vi) ORIGINAL SOURCE:
          (A) ORGANISM: Mycobacterium avium subspecies
               paratuberculosis

    (xi) SEQUENCE DESCRIPTION: SEQ ID NO:10:

GCACGGGGGG ACGTC                                                      15


(2) INFORMATION FOR SEQ ID NO:11:

     (i) SEQUENCE CHARACTERISTICS:
          (A) LENGTH: 15 base pairs
          (B) TYPE: nucleic acid
          (C) STRANDEDNESS: single
          (D) TOPOLOGY: linear

    (ii) MOLECULE TYPE: DNA (genomic)

   (iii) HYPOTHETICAL: NO

    (iv) ANTI-SENSE: NO

    (vi) ORIGINAL SOURCE:
          (A) ORGANISM: Mycobacterium avium subspecies
               paratuberculosis

    (xi) SEQUENCE DESCRIPTION: SEQ ID NO:11:

GCAAGAGGGG ACGTC                                                      15


(2) INFORMATION FOR SEQ ID NO:12:

     (i) SEQUENCE CHARACTERISTICS:
          (A) LENGTH: 15 base pairs
          (B) TYPE: nucleic acid
          (C) STRANDEDNESS: single
          (D) TOPOLOGY: linear

    (ii) MOLECULE TYPE: DNA (genomic)

   (iii) HYPOTHETICAL: NO

    (iv) ANTI-SENSE: NO

    (vi) ORIGINAL SOURCE:
          (A) ORGANISM: Mycobacterium avium subspecies
               paratuberculosis

    (xi) SEQUENCE DESCRIPTION: SEQ ID NO:12:

GCAAGGGGGG ACGTC                                                      15


(2) INFORMATION FOR SEQ ID NO:13:

     (i) SEQUENCE CHARACTERISTICS:
          (A) LENGTH: 20 base pairs
          (B) TYPE: nucleic acid
          (C) STRANDEDNESS: single
```

-continued (D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Mycobacterium avium (xi) SEQUENCE DESCRIPTION: SEQ ID NO:13:

AGAGTTTGAT CCTGGCTCAG 20

(2) INFORMATION FOR SEQ ID NO:14:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Mycobacterium avium (xi) SEQUENCE DESCRIPTION: SEQ ID NO:14:

ACCAGAAGAC ATGCGTCTTG 20

(2) INFORMATION FOR SEQ ID NO:15:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Mycobacterium avium subspecies paratuberculosis (xi) SEQUENCE DESCRIPTION: SEQ ID NO:15:

GACCGGCTAT CTGTGGAAC 19

(2) INFORMATION FOR SEQ ID NO:16:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Mycobacterium avium subspecies paratuberculosis -continued (xi) SEQUENCE DESCRIPTION: SEQ ID NO:16:

CTCGTCGGCT TGCACCTG 18